United States Patent
Flick et al.

(10) Patent No.: US 7,481,786 B2
(45) Date of Patent: Jan. 27, 2009

(54) DEVICE FOR ADMINISTERING COLD THERAPY TO ANKLES

(75) Inventors: Jonathan Wendell Flick, Mentor, OH (US); Jeffrey Alan Wilson, Cleveland Heights, OH (US); Max Benton, Avon, OH (US); Michael Ray Mancias, Cleveland, OH (US)

(73) Assignee: Wendell-Alan Ltd., Cleveland, OH (US)

( * ) Notice: Subject to any disclaimer, the term of this patent is extended or adjusted under 35 U.S.C. 154(b) by 299 days.

(21) Appl. No.: 11/307,751

(22) Filed: Feb. 21, 2006

(65) Prior Publication Data

US 2007/0197950 A1    Aug. 23, 2007

(51) Int. Cl.
  *A61F 13/00* (2006.01)
  *A61F 13/06* (2006.01)
  *A61F 5/00* (2006.01)
  *A61F 5/37* (2006.01)

(52) U.S. Cl. .............................. 602/65; 602/5; 602/13; 602/27; 602/60; 128/882

(58) Field of Classification Search .................... 602/1, 602/2, 5, 14, 23, 27, 41, 60–62, 65, 13; 128/882, 128/892; 607/96, 108–112, 114
  See application file for complete search history.

(56) References Cited

U.S. PATENT DOCUMENTS

| | | | |
|---|---|---|---|
| 4,556,055 A | 12/1985 | Bonner, Jr. | |
| 4,676,247 A | 6/1987 | Van Cleve | |
| 4,938,222 A | 7/1990 | Bier, Jr. | |
| 4,964,402 A * | 10/1990 | Grim et al. | 602/2 |
| 5,088,478 A | 2/1992 | Grim | |
| 5,113,877 A | 5/1992 | Johnson, Jr. et al. | |
| RE34,661 E * | 7/1994 | Grim | 602/27 |
| 5,366,439 A | 11/1994 | Peters | |
| 5,389,065 A * | 2/1995 | Johnson, Jr. | 602/27 |
| 5,395,399 A | 3/1995 | Rosenwald | |
| 5,409,500 A | 4/1995 | Dryek | |
| 5,415,624 A | 5/1995 | Williams | |
| 5,464,385 A | 11/1995 | Grim | |

(Continued)

FOREIGN PATENT DOCUMENTS

WO    92/15263    9/1992

(Continued)

*Primary Examiner*—Keri J. Nicholson
(74) *Attorney, Agent, or Firm*—Rankin, Hill & Clark LLP

(57) ABSTRACT

A device for administering cold therapy to a human ankle, and a method for administering cold therapy to a human ankle using the device. In accordance with the invention, two opposing flexible sheet members are connected via a web that spans a gap between them. At least one insert that includes a flexible, fluid-tight pouch containing at least a chilled, non-gaseous, temperature retaining fluid is releasably secured to one of the flexible sheet members. The insert is positioned adjacent to either the lateral or medial side of the human ankle. Bottom portions of each of the opposing flexible sheet members are secured to each other underneath the human's foot. Straps extending from the opposing flexible sheet members are drawn in opposite directions, one over the ankle ligaments on the top of the foot and another around the leg above the ankle, to secure the device to the human's ankle and thereby provide cold therapy and compression thereto.

12 Claims, 2 Drawing Sheets

U.S. PATENT DOCUMENTS

| | | |
|---|---|---|
| RE35,113 E | 12/1995 | Grim |
| 5,496,358 A | 3/1996 | Rosenwald |
| 5,743,867 A | 4/1998 | Hickling |
| 5,836,903 A | 11/1998 | Peters |
| 5,873,903 A | 2/1999 | Garcia |
| 5,921,243 A | 7/1999 | Shakoor |
| 6,139,486 A | 10/2000 | Matuszewski et al. |
| 6,440,159 B1 | 8/2002 | Edwards et al. |
| 6,582,383 B2 | 6/2003 | Horning |
| 6,589,272 B1 | 7/2003 | Sheikh |
| 6,617,485 B2 | 9/2003 | Herzberg |
| 7,060,086 B2 | 6/2006 | Wilson et al. |
| 2003/0171706 A1* | 9/2003 | Nelson ................. 602/65 |

FOREIGN PATENT DOCUMENTS

| | | |
|---|---|---|
| WO | 94/00087 | 1/1994 |
| WO | 98/49982 | 11/1998 |

* cited by examiner

DEVICE FOR ADMINISTERING COLD THERAPY TO ANKLES

BACKGROUND OF THE INVENTION

1. Field of Invention

The present invention relates to a device for administering cold therapy to ankles and a method of treating an injured ankle using the device.

2. Description of Related Art

Studies have shown that the most common sports-related injury is a lateral ankle sprain caused by a sudden, unexpected and relatively profound inversion of an athlete's foot. Athletes that participate in the sports of basketball, volleyball, soccer, and football are particularly susceptible to lateral ankle sprains due to the amount of jumping, cutting, and pivoting required, and due to the close body contact between athletes. Lateral ankle inversion injuries often occur as a result of the athlete's foot landing awkwardly after a step or jump and/or as a result of the athlete stepping on another athlete's foot. Many athletes will characterize an injury of this type as "rolling" their ankle.

The anatomy of the ankle places the lateral side of the ankle at a higher risk for sprain injury than the medial side. The distal end of the fibula (i.e., the lateral malleolus) extends further inferiorly than the distal end of the tibia (i.e., the medial malleolus). Thus, there is less bony stability on the lateral side of the ankle as compared to the medial side of the ankle. On the lateral side of the ankle, three ligaments provide stability, namely: the anterior talofibular ligament ("ATFL"); the calcaneofibular ligament ("CFL"); and the posterior talofibular ligament ("PTFL"). In a lateral ankle sprain, at least one, and more typically two or more, of these three ligaments are injured, with the severity of the injury ranging from a slight degree of tearing to rupture.

The generally accepted first aid treatment regimen for a lateral ankle sprain and other ankle injuries is often referred to by the acronym "RICE", which stands for rest, ice, compression, and elevation. Rest is prescribed because continued activity can cause further injury to the ankle, thereby delaying the healing process, increasing pain, and stimulating internal bleeding. Ice is prescribed because blood vessels contract when exposed to cold temperatures, which helps reduce swelling in the ankle and also helps to reduce the extent of internal bleeding from injured capillaries and blood vessels. Compression is prescribed because it tends to hasten healing time by reducing swelling around injury. And, elevation of the ankle above the heart is prescribed because it tends to reduce swelling and also tends to reduce pain.

Although ice is specifically identified by name in the RICE acronym, ice is not generally considered to be the best material for providing cold therapy to ankles. Ice can cause discomfort when placed between a compressive wrap and an injured ankle because it is a rigid non-conforming solid material. Furthermore, ice is difficult to position on an injured ankle, and tends to melt quickly, which results in a loss of the desired cold treatment and/or frequent disturbance of the injured ankle to apply more ice. In view of these and other disadvantages, ice alternatives are typically used to provide cold therapy treatment to injured ankles.

In recent years, temperature-retaining gel-filled thermal packs have been used instead of ice to provide cold therapy to injured ankles. The gels used in such packs tend to remain cold for a longer period of time than ice, and such gels also preferably remain viscous at low temperatures, which allow them to more comfortably conform to the contours of the injured ankle when placed between a compressive wrap and the injured ankle.

Conventional gel-filled thermal treatment packs generally consist of a substantially flat flexible envelope that has been filled with a temperature-retaining gel material. Pre-chilled "flat packs" of this type are typically pressed into contact with an injured ankle and over-wrapped with a suitable material such as an elongated elastic bandage to hold it in place and provide compression to the injured ankle. Some gel-filled thermal treatment packs are provided with straps or other means of securing the flat pack in contact with the injured ankle.

Flat packs such as described, while widely used to provide first aid treatment to injured ankles and other limbs, present certain problems and disadvantages. One problem with flat packs is that they do not provide targeted cold therapy specifically to the injured ligaments of the ankle. Such devices are intended for general use, and thus provide cold therapy to large areas. When applied to an injured ankle, flat packs administer cold treatment to non-injured portions of the ankle such as, for example, the lateral malleolus, which projects away from the ankle. The application of cold therapy to bony portions of the ankle such as the lateral malleolus can cause discomfort, which will cause the athlete to remove the cold therapy and thereby adversely affect healing of the injured ligaments.

It will be appreciated that in some instances, the ankle sprain will occur to the medial ligaments rather than, or in addition to, the lateral ligaments. In such circumstances, it has been necessary to apply two flat packs to the injured ankle, which make placement and retention of the flat packs very difficult. It is difficult and time consuming to accurately secure a flat pack to an injured ankle using an elastic wrap, and it is even more difficult when two flat packs must be secured.

BRIEF SUMMARY OF THE INVENTION

The present invention provides a device for administering cold therapy to a human ankle, and a method for administering cold therapy to a human ankle using the device. In accordance with the invention, two opposing flexible sheet members are connected via a web that spans a gap between them. At least one insert that comprises a flexible, fluid-tight pouch containing at least a chilled, non-gaseous, temperature retaining fluid is releasably secured to one of the flexible sheet members. The insert is positioned adjacent to either the lateral or medial side of the human ankle. Bottom portions of each of the opposing flexible sheet members are secured to each other underneath the human's foot. Straps extending from the opposing flexible sheet members are drawn in opposite directions, one over the ankle ligaments on the top of the foot and another around the leg above the ankle, to secure the device to the human's ankle and thereby provide cold therapy and compression thereto.

The foregoing and other features of the invention are hereinafter more fully described and particularly pointed out in the claims, the following description setting forth in detail certain illustrative embodiments of the invention, these being indicative, however, of but a few of the various ways in which the principles of the present invention may be employed.

DETAILED DESCRIPTION OF THE INVENTION

Figure 1:
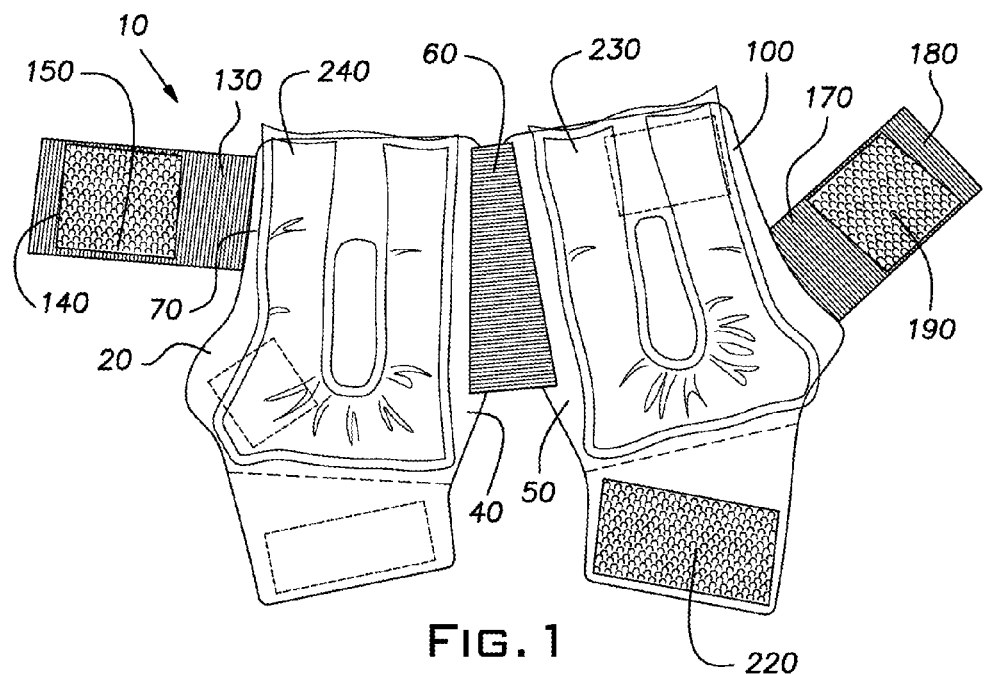
FIG. 1 is a view showing the inner side of a preferred embodiment of a device for providing cold therapy to ankles according to the invention.
Figure 2:
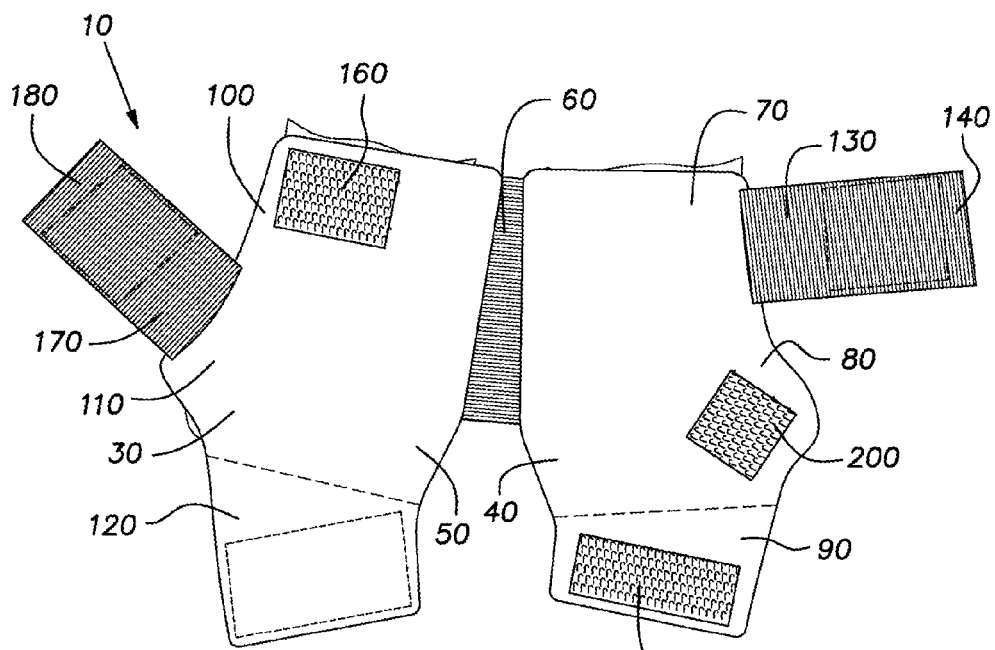
FIG. 2 is a view showing the outer side of the device for providing cold therapy to ankles shown in FIG. 1.

FIGS. 1 and 2 show the inner side 20 and the outer side 30, respectively, of the presently most preferred embodiment of a device 10 for providing cold therapy to a human ankle according to the invention. The term "inner side", as used in this context, refers to the side of the device 10 that is positioned adjacent to a human's ankle when the device 10 is secured thereto, whereas the term "outer side" refers to the side of the device 10 that is exposed when the device 10 is secured to a human ankle.

The device 10 comprises a first flexible sheet member 40 and an opposing second flexible sheet member 50. The first and second flexible sheet members 40, 50 are preferably formed of one or more layers of a fabric material such as woven nylon or canvas, which can be stitched together to form a flexible sheet. In a preferred embodiment of the invention, the first and second flexible sheet members 40, 50 are formed of two layers of nylon sandwiching a thin closed-cell foam sheet. The perimeter contours of the first and second flexible sheet members 40, 50 are configured to conform to and cover either a lateral or medial side of a human's ankle and an additional area from about mid-foot to the leg above the human's ankle.

A web 60 is connected to both the first flexible sheet member 40 and the second flexible sheet member 50. The web 60 preferably spans a gap or space between the first flexible sheet member 40 and the second flexible sheet member 50. It will be appreciated, however, that it is possible to form a device according to the invention having no gap or space between the first and second flexible sheet members (i.e., the first and second flexible sheet members are in contact with each other), or a device according to the invention wherein the first flexible sheet member and the second flexible sheet member are formed from a single sheet of material (i.e., they are integral, and no web spans them). The web 60 can, but need not be, formed of an elastic material. In the presently most preferred embodiment of the invention, the web 60 is formed of an elastic material that stretches in a vertical direction (i.e., stretchable in a direction parallel to the human's leg) when the device is secured to a human ankle.

The first flexible sheet member 40 comprises an upper portion 70, an intermediate portion 80 and a bottom portion 90. Likewise, the second flexible sheet member 50 comprises an upper portion 100, an intermediate portion 110 and a bottom portion 120. A first elastic strap 130 extends from the upper portion 70 of the first flexible sheet member 40. The first elastic strap 130 has an end portion 140 that is configured to releasably fasten to the upper portion 100 of the second flexible sheet member 50. Hook and loop fasteners are the preferred means of securing the end portion 140 of the first elastic strap 130 to the upper portion 100 of the second flexible sheet member 50. Preferably, the loop portion 150 of the hook and loop fastener is attached to the end portion 140 of the first elastic strap 130 and the hook portion 160 is attached to the outer side 30 of the second flexible sheet member 50, although this arrangement is not critical.

A second elastic strap 170 extends from the intermediate portion 110 of the second flexible sheet member 50. The second elastic strap 170 has an end portion 180 that is configured to releasably fasten to the intermediate portion 80 of the first flexible sheet member 40. It will be appreciated that the first elastic strap 130 pulls from one side of the ankle (lateral or medial) whereas the second elastic strap 170 pulls from the other side of the ankle. The straps 130, 170 do not cross over each other, but pull from opposite sides of the ankle around a front part of the ankle and/or leg. The web 60 is positioned adjacent to the rear portion of the leg, above the rear portion of the calcaneus.

As in the case of the first elastic strap 130, hook and loop fasteners are the preferred means of securing the end portion 180 of the second elastic strap 170 to the intermediate portion 80 of the first flexible sheet member 40. Preferably, the loop portion 190 of the hook and loop fastener is attached to the end portion 180 of the second elastic strap 170 and the hook portion 200 is attached to the outer side 30 of the first flexible sheet member 40, although this arrangement is not critical. The first and second elastic straps 130, 170 are preferably formed of an elastic material that is stretchable in a direction away from the attachment point of the straps 130, 170 to their respective first or second flexible sheet members 40, 50. The first and second elastic straps 130, 170 are also preferably relatively wide, having a width dimension that is greater than or equal to about 3.0 inches.

The bottom portion 90 of the first flexible sheet member 40 is configured to be releasably securable to the bottom portion 120 of the second flexible sheet member. In the preferred embodiment, a hook and loop fastener system is used for this purpose. For example, the hook portion 210 of the hook and loop fastener system can be stitched or otherwise secured to the outer side 30 of the bottom portion 90 of the first flexible sheet 40, with the mating loop portion 220 being stitched or otherwise secured to the inner side 20 of the bottom portion 120 of the second flexible sheet 50. The bottom portions 90, 120 of the first and second flexible sheet members 40, 50 are intended to be fastened to each other beneath the foot of the human when the device is secured to the human's ankle.

At least a first insert 230 is releasably fastened to one of the first flexible sheet member 40 or the second flexible sheet member 50. More preferably, a second insert 240 is releasably fastened to the other of the first flexible sheet member 40 or the second flexible sheet member 50 to which the first insert 230 is not releasably fastened. Preferably, the second insert 240 is identical in size and construction to the first insert 230, except that it has a mirror image shape. Thus, the following description of the first insert 230 applies to the second insert 240.

Figure 3:
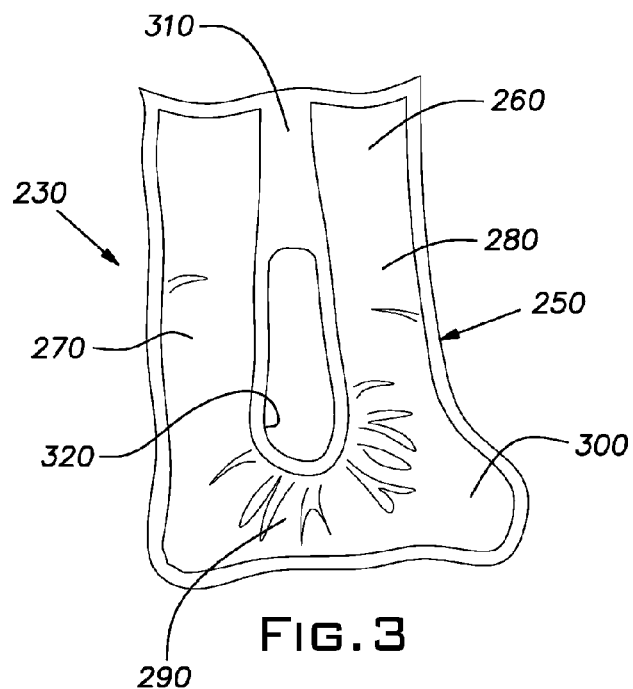
FIG. 3 is detailed perspective view of a preferred embodiment of a gel pack for use in a device for providing cold therapy to ankles according to the invention.
Figure 4:
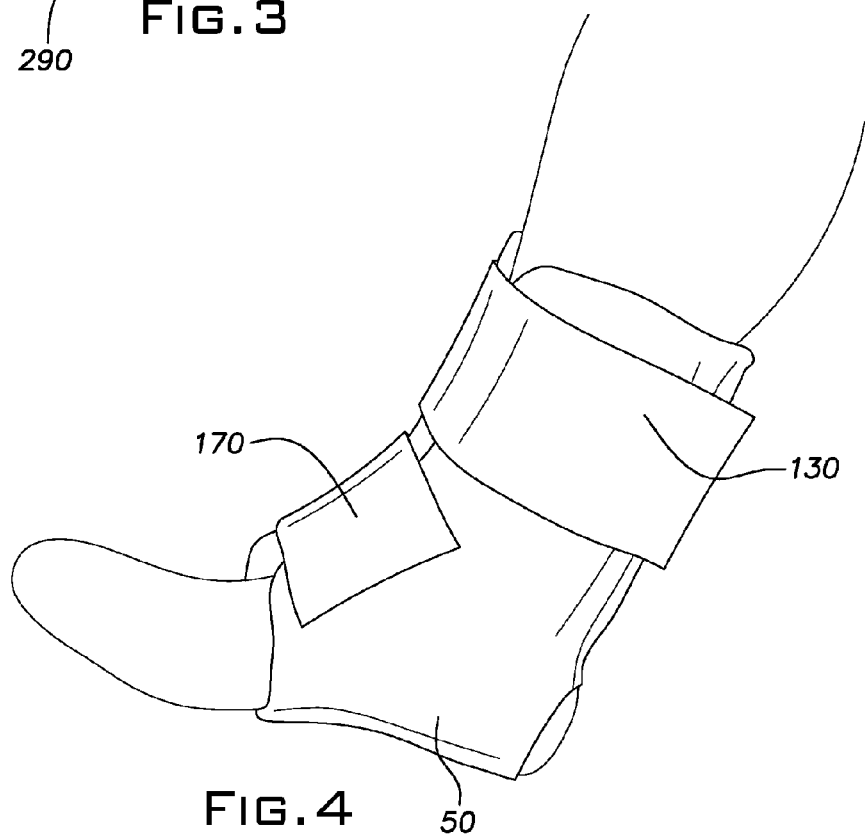
FIG. 4 is a perspective view of a device for providing cold therapy to ankles according to the invention disposed on an ankle.

With reference to FIG. 3, the first insert 230 has a first side 250 that is configured to releasably fasten to an inner side 20 of one of the first flexible sheet member 40 or the second flexible sheet member 50. In the preferred embodiment of the invention, one of a hook portion or a loop portion of a hook and loop fastening system is secured to the first side 250 of the first insert 230 (e.g., using adhesive). The mating portion of the hook and loop fastening system is secured to the inner side 20 of either the first flexible sheet member 40 or the second flexible sheet member 50.

The first insert 230 comprises a flexible, fluid-tight pouch 260 containing at least a non-gaseous temperature retaining fluid. Throughout the instant specification and in the appended claims, the term "temperature-retaining fluid" means any non-gaseous material that changes shape or direction uniformly in response to an external force imposed upon it and that has the capacity to transfer cold therapy to an ankle.

The term applies not only to liquids, but also to finely divided solids having such properties. Preferably, the temperature-retaining fluid is a gel, and more preferably a water-based gel.

Water-based gels can be formulated so as to provide a temperature-retaining fluid that is more viscous than water and does not become a hard solid within the temperature range of from 0° F. and 32° F. Such gels can conform to the contours of an ankle more comfortably than ice. In addition, such gels tend to retain their desired thermal properties for a longer period of time than ice. The composition of the gel is not per se critical, but preferably a non-toxic formulation is used to minimize potential injury in the event of exposure.

In the presently most preferred embodiment of the invention, no solids of any kind are dispersed in the temperature-retaining fluid. However, it will be appreciated that any relatively small substantially free-flowing solid structure could be dispersed in the temperature-retaining fluid, if desired. Suitable solid materials include, for example, water-filled capsules, inorganic particulates (e.g., sand and/or ceramic particles), spherical structures (e.g., glass and/or metal spheres), magnets and combinations thereof. Such structures can be used to extend the period of time during which the temperature-retaining fluid remains cold or provide other treatment benefits.

The pouch 260 is preferably formed between two layers of a film of flexible material that remains flexible over a relatively broad temperature range of from about 0° F. to about 70° F. A large number of polymeric films that remain flexible over such a temperature range are known in the art. It will be appreciated that polymeric films used in the invention can be single layer films or multi-layer structures.

Preferably, the film of flexible material exhibits a Shore A durometer hardness of greater than or equal to 85 as measured in accordance with the ASTM 2240.00 standard. More preferably, the continuous film of flexible material exhibits a Shore A durometer hardness of 90±5 as measured in accordance with the ASTM 2240.00 standard. Films possessing such properties are advantageously puncture resistant yet remain flexible.

Each layer of the film of flexible material can have a thickness of from about 3 to about 15 mils. More preferably, the continuous film of flexible material can have a thickness of 5±2 mils. It will be appreciated that film thickness is not per se critical, and that a variety of film thicknesses can be used to fabricate a thermal pack in accordance with the invention.

In the presently most preferred embodiment of the invention, each layer of the film of flexible material comprises a 5 mil thick copolymer of polyester and polyurethane having a Shore A durometer hardness of about 90 as measured in accordance with the ASTM 2240.00 standard. This film provides several advantages. It can be heat sealed to itself, which facilitates fabrication of the insert 230. It does not irritate human skin on contact. And, it remains smooth and flexible over the useful temperature range.

The temperature-retaining fluid is retained in the pouch 260 in the form of a pair of spaced apart tubular sections 270, 280. The pouch 260 also preferably includes a lower section 290 that spans the distance between the spaced apart tubular sections 270, 280. The pouch 260 also includes a flap section 300 that extends away from one side of the lower section 290. Thus, the pouch 260 portion of the insert 230 is generally U-shaped, but features a flap section 300 that extends from a side of the lower section 290. Preferably, the spaced apart tubular sections 270, 280, lower section 290 and flap section 300 of the pouch 260 are in fluid communication with each other. It will be appreciated, however, that each section can be formed separate and distinct from the other sections, as desired.

The spaced apart tubular sections 270, 280 can be kept in the proper orientation relative to each other using a bridging section 310 of flexible film. It is preferable, however, that if a bridging section 310 is present, an opening 320 is formed between the bridging section 310 and the lower section 290 of the pouch to receive the lateral or medial malleolus when the device 10 is secured to the human ankle. The generally U-shaped pouch 260 allows for cold therapy to be applied to the ligaments of the ankle. When applied adjacent to the lateral side of the ankle, the flap section 300 provides cold therapy to the anterior talofibular ligament and the lower section 290 provides cold therapy to the calcaneofibular ligament and the posterior talofibular ligament. The tubular sections 270, 280 apply cold therapy to the peroneal tendon and other muscles, tendons and soft tissues on either side of the lateral malleolus that can be strained due to inversion of the ankle.

The method for providing cold therapy to a human ankle according to the invention involves applying a device 10 to the human ankle. A pre-chilled first insert 230 is fastened to an inner side of one of the first flexible sheet member 40 or the second flexible sheet member 50. It will be appreciated that the shape of the first insert 230 (i.e., the orientation of the flap section 300) and whether the first insert 230 is fastened to the first flexible sheet member 40 or the second flexible sheet member 50 will be determined by whether the lateral or medial side of the left or right ankle is to be treated with cold therapy. It is important that the flap section 300 of the first insert be oriented toward the front of the foot when the malleolus (lateral or medial) is disposed between the tubular sections 270, 280 and above the lower section 290 of the pouch 260. More preferably, a second insert 240 is also secured to the inner side 20 of the other of the first flexible sheet member 40 or the second flexible sheet member 50 to which the first insert 230 is not fastened. The flap section of the second insert must also be oriented toward the front of the foot when the malleolus (lateral or medial) is disposed between the tubular sections and above the lower section of the pouch. The second insert 240 does not necessarily need to be pre-chilled, but can be used to provide comfort to the wearer. However, in the most preferred embodiment of the invention, the second insert 240 is also pre-chilled, and thus the device 10 can simultaneously provide cold therapy to both the lateral and medial ligaments and lower soft tissues of the lower leg and ankle. It is possible, but not preferable, to position one or both of the inserts 230, 240 adjacent to the ankle, and then press the inner side 20 of the device 10 against the insert(s) 230 240.

The bottom portion 90 of the first flexible sheet member 40 must be fastened to the bottom portion 120 of the second flexible sheet member 50. This can be done before the device 10 is positioned adjacent to the ankle, or after the device 10 has been placed adjacent to the ankle. Preferably, the device 10 is positioned such that the lateral malleolus and the medial malleolus are disposed between the tubular sections 270, 280 of the inserts 230, 240, then the bottom portions 90, 120 of the flexible sheet members 40, 50 are fastened to each other underneath the foot.

The second elastic strap 170 is drawn over the top of the foot and the end portion 180 is secured to the intermediate portion 80 of the first flexible sheet member 40 such that the second elastic strap 170 wraps over the top of the foot and provides compression on at least the flap section 300 of the first insert 230. The first elastic strap 130 is drawn around the leg above the ankle and secured to the upper portion 100 of the second flexible sheet member 50 such that the first elastic strap 130 wraps around the leg and provides compression above the ankle. It will be appreciated that the order in which the straps are secured is not critical, and that any order can be used. Once the device 10 is positioned on the ankle, fine adjustments can be made to apply the desired amount of compression on the desired locations on the ankle simply by unhooking and rehooking the hook and loop fastening systems. In some instances, it may be desirable to provide cold therapy to the top portion of a foot. In such instances, one can place a conventional pre-chilled flat pack on the top of the foot, and use the first and second elastic straps to secure the flat pack on the top of the foot. A flat pack measuring about 3"×6" is particularly suitable for this use.

It is often desirable to dispose a fabric layer between the ankle and the insert(s), particularly when the insert(s) have been pre-chilled. The fabric layer acts as an insulation layer, which prevents frostbite and prolongs the time the device can be comfortably worn. The fabric layer can be wrapped around the ankle prior to applying the device or, more preferably, the device can be applied over a sock or stocking.

The device and method for providing cold therapy to ankles according to the invention is particularly suitable for use in treating sports related injuries. Several pre-chilled inserts can be stored in a cooler or other suitable refrigerated container together with ice or other cold packs in anticipation of being needed to treat an injury. When an athlete sustains an ankle injury, one or more insert(s) can be removed from the cooler and fastened to the inner side of the device, as appropriate. The athlete can remove his or her shoe, and the device can be applied immediately to reduce swelling, pain and hasten healing at the site of the injury. The device can be applied very quickly and very accurately with little movement of the ankle. Devices and inserts of various sizes can be kept on hand to treat the ankles of individuals of various height and age.

In addition to be useful for treating sports related injuries, the device according to the invention can be used in a variety of other applications. For example, the device can be used in physical therapy, rehabilitation and/or pain relief applications. Furthermore, the device can be used in geriatric care and in post-operative recovery. The cooling effect is soothing, and can be used to provide comfort to individuals who have tired feet and ankles. Applicants have found that the device not only cools the ankle areas directly in contact with the pouch or pouches, after about 10 minutes of use, it also provides soothing relief virtually to the entire foot and lower leg area. In addition, the device can be used to provide compression to an ankle only (i.e., compression without cold therapy). In such applications, one or more pouches that have not been pre-chilled are used.

Additional advantages and modifications will readily occur to those skilled in the art. Therefore, the invention in its broader aspects is not limited to the specific details and illustrative examples shown and described herein. Accordingly, various modifications may be made without departing from the spirit or scope of the general inventive concept as defined by the appended claims and their equivalents.

What is claimed is:

1. A device for administering cold therapy to ligaments of a human ankle, the device comprising:
a first flexible sheet member having an upper portion, an intermediate portion and a bottom portion, the first flexible sheet member being adapted to conform to and cover one of:
a lateral side of the ankle and an additional area from about mid-foot to the leg above the ankle, or
a medial side of the ankle and an additional area from about mid-foot to the leg above the ankle;
a second flexible sheet member having an upper portion, an intermediate portion and a bottom portion, the second flexible sheet member being adapted to conform to and cover the other of:
the lateral side of the ankle and an additional area from about mid-foot to the leg above the ankle, or
the medial side of the ankle and an additional area from about mid-foot to the leg above the ankle;
a web connected to both the first flexible sheet member and the second flexible sheet member, the web spanning a gap between the first flexible sheet member and the second flexible sheet member, the web being adapted to be positioned adjacent to a rear portion of the leg;
a first elastic strap extending from the upper portion of the first flexible sheet member, the first elastic strap being adapted to be drawn around the leg above the ankle, the first elastic strap having an end portion configured to releasably fasten to the upper portion of the second flexible sheet member;
a second elastic strap extending from the intermediate portion of the second flexible sheet member, the second elastic strap being adapted to be drawn over the top of the foot, the second elastic strap having an end portion configured to releasably fasten to the intermediate portion of the first flexible sheet member;
a fastener for releasably securing the bottom portion of the first flexible sheet to the bottom portion of the second flexible sheet beneath the foot of the human; and
a first insert comprising a flexible, fluid-tight pouch containing at least a non-gaseous temperature retaining fluid, the pouch comprising a pair of spaced apart tubular sections, a lower section spanning the distance between the spaced apart tubular sections, and a flap section extending away from the lower section, the first insert having a first side configured to releasably fasten to one of the first flexible sheet member or the second flexible sheet member such that one of the lateral malleolus or the medial malleolus can be disposed between the pair of spaced apart tubular sections above the lower section and the flap can be oriented toward the front of the foot, wherein the spaced apart tubular section, lower section and flap section of the pouch of the first insert are in fluid communication with each other.

2. The device according to claim 1 further comprising a second insert comprising a flexible, fluid-tight pouch containing at least a non-gaseous temperature retaining fluid, the pouch comprising a pair of spaced apart tubular sections, a lower section spanning the distance between the spaced apart tubular sections, and a flap section extending away from the lower section, the second insert having a first side configured to releasably fasten to the other of the first flexible sheet member or the second flexible sheet member such that one of the lateral malleolus or the medial malleolus can be disposed between the pair of spaced apart tubular sections above the lower section and the flap can be oriented toward the front of the foot, wherein the spaced apart tubular section, lower section and flap section of the pouch of the second insert are in fluid communication with each other.

3. The device according to claim 1 wherein the first and second flexible sheet members are formed of a polymeric fabric.

4. The device according to claim 3 wherein the polymeric fabric is nylon.

5. The device according to claim 1 wherein the web spanning the gap between the first flexible sheet member and the second flexible sheet member is formed of an elastic material.

6. The device according to claim 1 wherein the first elastic strap is releasably fastened to the second flexible sheet member using a hook and loop fastening system.

7. The device according to claim 1 wherein the second elastic strap is releasably fastened to the first flexible sheet member using a hook and loop fastening system.

8. The device according to claim 1 wherein the fastener for releasably securing the bottom portion of the first flexible sheet to the bottom portion of the second flexible sheet is a hook and loop fastening system.

9. The device according to claim 1 wherein the non-gaseous temperature retaining fluid in the first insert is a water-based gel having a viscosity greater than that of water and a freezing point below that of water.

10. The device according to claim 1 wherein the first insert is releasably fastened to one of the first flexible sheet member or the second flexible sheet member using a hook and loop fastener system.

11. A method for providing cold therapy to a human ankle comprising:
 providing a device comprising:
  a first flexible sheet member having an upper portion, an intermediate portion and a bottom portion;
  a second flexible sheet member having an upper portion, an intermediate portion and a bottom portion;
  a web connected to both the first flexible sheet member and the second flexible sheet member, the web spanning a gap between the first flexible sheet member and the second flexible sheet member;
  a first elastic strap extending from the upper portion of the first flexible sheet member, the first elastic strap having an end portion configured to releasably fasten to the upper portion of the second flexible sheet member;
  a second elastic strap extending from the intermediate portion of the second flexible sheet member, the second elastic strap having an end portion configured to releasably fasten to the intermediate portion of the first flexible sheet member; and
  a fastener for releasably securing the bottom portion of the first flexible sheet member to the bottom portion of the second flexible sheet member;
 fastening a first side of a first insert to one of the first flexible sheet member or the second flexible sheet member, the first insert comprising a flexible, fluid-tight pouch containing at least a chilled, non-gaseous, temperature retaining fluid, the pouch comprising a pair of spaced apart tubular sections, a lower section spanning the distance between the spaced apart tubular sections, and a flap section extending away from the lower section, wherein the spaced apart tubular section, lower section and flap section of the pouch of the first insert are in fluid communication with each other;
 positioning an opposing second side of the first insert adjacent to a lateral side of the human ankle such that the lateral malleolus is disposed between the spaced apart tubular sections and the flap section is disposed adjacent to at least the anterior talofibular ligament;
 securing the bottom portion of the first flexible sheet to the bottom portion of the second flexible sheet underneath the foot;
 securing the second elastic strap to the intermediate portion of the first flexible sheet member such that the second elastic strap wraps over the top of the foot and provides compression on at least the flap section of the first insert; and
 securing the first elastic strap to the upper portion of the second flexible sheet member such that the first elastic strap wraps around the leg and provides compression above the ankle.

12. The method according to claim 11 further comprising:
 fastening a first side of a second insert to the other of the first flexible sheet member or the second flexible sheet member to which the first insert is not fastened, the second insert comprising a flexible, fluid-tight pouch containing at least a chilled, non-gaseous, temperature retaining fluid, the pouch comprising a pair of spaced apart tubular sections, a lower section spanning the distance between the spaced apart tubular sections, and a flap section extending away from the lower section, wherein the spaced apart tubular section, lower section and flap section of the pouch of the second insert are in fluid communication with each other; and
 positioning an opposing second side of the second insert adjacent to a medial side of the human ankle such that the medial malleolus is disposed between the spaced apart tubular sections.

* * * * *